United States Patent [19]
Daikuzono

[11] Patent Number: 5,151,097
[45] Date of Patent: Sep. 29, 1992

[54] LASER LIGHT EMITTER

[75] Inventor: Norio Daikuzono, Ichihara, Japan

[73] Assignee: S.L.T. Japan Co., Ltd., Tokyo, Japan

[21] Appl. No.: 573,563

[22] Filed: Aug. 28, 1990

[30] Foreign Application Priority Data

Sep. 1, 1989 [JP] Japan ................. 1-227092

[51] Int. Cl.$^5$ ............................................. A61B 17/35
[52] U.S. Cl. ........................................... 606/15; 606/16; 606/17
[58] Field of Search ................... 606/2, 7, 10–16; 128/395–398; 219/121.6

[56] References Cited

U.S. PATENT DOCUMENTS

| | | |
|---|---|---|
| 4,126,136 | 11/1978 | Auth et al. |
| 4,240,431 | 12/1980 | Komiya .............. 606/15 |
| 4,249,533 | 2/1981 | Komiya .............. 606/15 |
| 4,266,547 | 5/1981 | Komiya .............. 606/15 |
| 4,273,127 | 6/1981 | Auth et al. |
| 4,693,244 | 9/1987 | Daikuzono . |
| 4,736,743 | 4/1988 | Daikuzono . |

FOREIGN PATENT DOCUMENTS 63-216579  9/1988  Japan .
2-34161   2/1990  Japan .

*Primary Examiner*—Peter A. Aschenbrenner
*Attorney, Agent, or Firm*—Lowe, Price, Le Blanc & Becker

[57] ABSTRACT

A laser light emitter is provided for use in a medical treatment, particularly excision of a prominence of an animal organism. The laser light emitter has an excision portion, wherein a part of said excision portion includes a laser light emitting portion which is capable of emitting laser light in the direction for excision of the prominence. The emitter also includes a light emission-intercepting member on the side opposite to the direction for excision of the prominence in order to prevent laser light emission. The laser light emitting portion is optically connected with a laser light generator. By using such a laser light emitter, safe excision of the prominence can be made without giving a shock to the human body or a burn, if laser light is emitted under the presence of a physiological salt solution. In addition, it is possible to remove the prominence while controlling bleeding by regulating the quantity of laser light emission and the ability of hemostasis by laser light.

11 Claims, 5 Drawing Sheets

LASER LIGHT EMITTER

BACKGROUND OF THE INVENTION

This invention relates to a laser light emitter in use for excision of a prominence of living tissue of animal organisms.

A known high frequency scalpel has been used in excision of a prominence of living tissue, such as a prostate. For example, a conventional high frequency scalpel has a hexagonal wire 51 projecting in front of a holder 50 as shown in FIG. 11, and high frequency current flows through the wire 51.

When such apparatus for excision is used, wire 51 is so positioned that a prominence is disposed within the wire 51, and then high frequency current flows through wire 51 so as to cauterize and remove the prominence by heat.

However, this kind of a high frequency snare has a disadvantage fundamentally. Namely, when a prominence, that is an affected part, is removed under the presence of physiorogical salt solution, electricity flowing through physiorogical salt solution occasionally gives a shock to the human body or a burn near the affected part.

This forces an operator to replace physiological salt solution with distilled water during medical treatment, making it impossible to remove a prominence while stopping bleeding.

OBJECTS OF THE INVENTION

The general object of the present invention is providing a laser light emitter which can perform excision under the presence of physiorogical salt solution and can perform excision with controlling bleeding.

SUMMARY OF THE INVENTION

The present invention provides a laser light emitter for excision of protruding tissue of an animal organism, the emitter comprising:

an optical transmission element having a holding portion through which light is transmitted into a bent portion that has an end surface and a side surface; and a light impervious material covering a first portion of said side surface of the bent portion of the optical transmission element, such that a second portion of said side surface of the bent portion of the optical transmission element is uncovered, whereby laser light applied to the optical transmission element will be emitted from the uncovered second portion of said side surface of the bent portion to impinge on and excise protruding tissue.

DETAILED DESCRIPTION OF THE INVENTION

According to the present invention, a prominence is removed by emitting laser light.

Accordingly, safe excision of the prominence can be made without giving a shock to the human body or a burn, if laser light is emitted under the presence of physiological salt solution.

In addition, it is possible to remove the prominence while controlling bleeding by regulating quantity of laser light emission and the ability to effect hemostasis by laser light. Therefore a laser light emitter according to the present invention is highly effective for excision of hemorrhagic organism.

Moreover, a laser light emitter in the present invention is capable of being used in an operation by using an endoscope as well as a surgical operation.

The present invention is described more particularly hereinafter.

FIGS. 1 to 4 show the first embodiment. An optical fiber 1 is covered with a metal member, for example a stainless-steel tube 2 to form an element having a holding portion through which laser light is transmitted with a bent portion that has a side surface and ends in an end surface.

The excision instrument 10, in the preferred embodiment provides parallel holding portions 11A,11B and a ring-shaped bent portion 12 corresponding to the excision means in the present invention continuously connected with the holding portion 11A and the holding portion 11B.

The ring-shaped bent portion 12 projects downward in the shape of a letter U from the ends of the holding portions 11A,11B. Either side of optical fiber 1, for example the end of the optical fiber 1 covered with the holding portion 11A, is optically connected with a laser light generator (not illustrated).

A part of the ring-shaped portion 12 composes a laser light emitting portion L which is exposed to emit laser light substantially in the lateral direction C (FIG. 2) for excision of the prominence Mx. The rest of the ring-shaped vent portion 12 composes a light emission-intercepting member covering the side opposite the direction C for excision, in order to shut off the laser light emission.

To be more specific, the core of the optical fiber 1 is exposed at the part of ring-shaped portion 12 where it is not covered by stainless steel tube 2 so as to form the emitting portion L. The rest of the ring-shaped vent portion 12 is covered with the stainless-steel tube 2 to form the laser light emission-intercepting member in the present invention.

Figure 2:
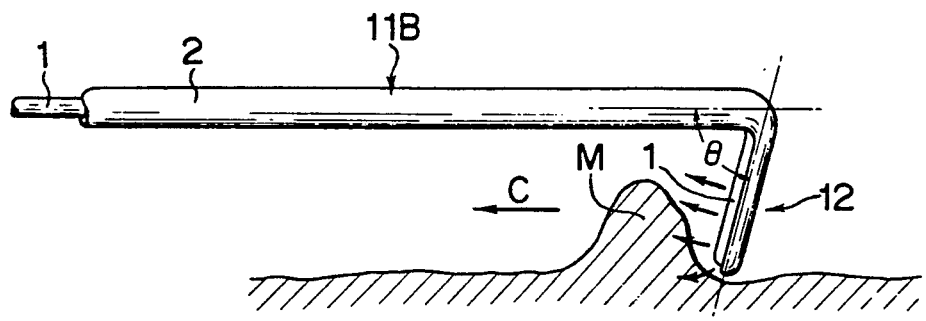
FIG. 2 is a front view of the embodiment of FIG.1.
Figure 3:
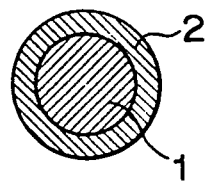
FIG. 3 is a sectional view of the embodiment of FIG. 1 taken on line III—III.
Figure 4:
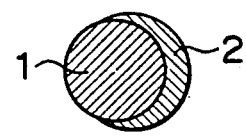
FIG. 4 is a sectional view of the embodiment of FIG. 1 taken on line IV—IV.

In such an apparatus, laser light generated from a laser light generator is transmitted into the optical fiber 1, but where fiber 1 is covered with the stainless-steel tube 2 laser light is not emitted. Accordingly, a part of the stainless-steel tube 2 on the emitting portion L is opened in the lateral direction C for excision such that a laser light is emitted from the exposed portion of the core of the optical fiber 1, as illustrated in FIG. 2. Laser light is irradiated to the prominence M, and excision is done from the root of the prominence M by the excision ability of laser light. An operator generally holds the instrument for excision in the present invention on the holding portions 11A,11B, and then moves the instrument in the direction C for excision to exert an excision force.

In the above-described embodiment, the core of the optical fiber 1 is directly covered with the stainless-steel tube 2; however, the core of the optical fiber 1 may be covered with claddding. In such a case the core of the optical fiber 1 is exposed by removing the cladding on at least the emitting portion L.

Figure 5:
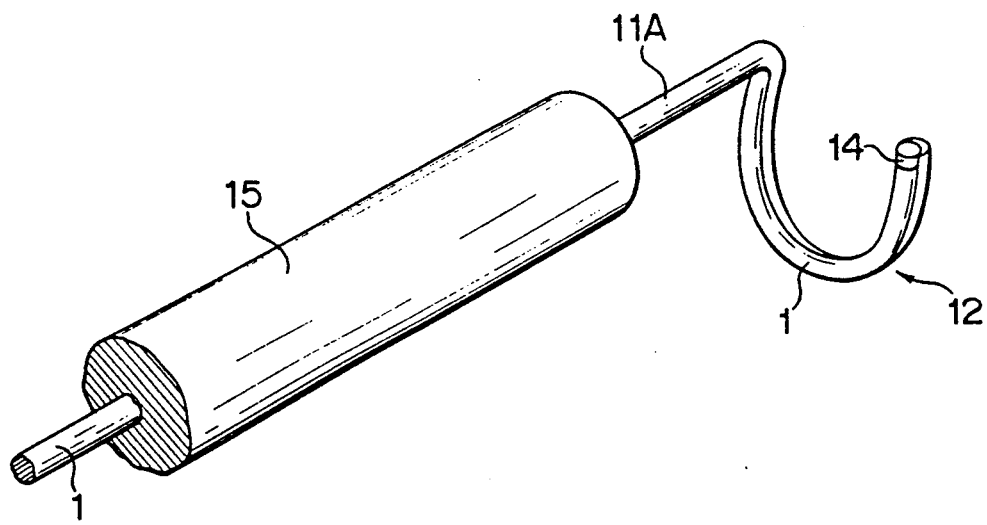
FIG. 5 is a perspective view of the second embodiment of a laser light emitter according to the present invention.

In the first embodiment, the angle θ defined by the holding portion 11A,11B and the emitting portion L is 45°–120°, preferably In the first embodiment, there are two of the parallel holding portions 11A,11B. Alternatively only the holding portion 11A is formed, and the emitting portion L is capable of being formed at the end of the holding portion 11A, as shown in FIG. 5. The part designated by numeral 15 is a holder, provided if needed.

Figure 6:
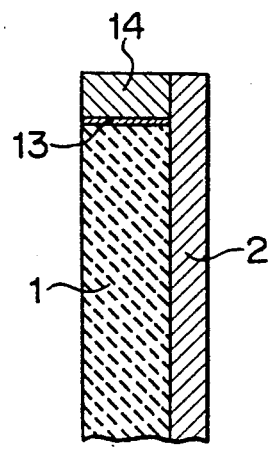
FIG. 6 is a vertical sectional view of a part of the second embodiment.

Moreover, according to the second embodiment in FIG. 5 and FIG. 6, a laser light reflecting portion 13 is provided at the end of the emitting portion L. The reflecting portion 13 prevents laser light from being emitted at the end of the optical fiber 1, and laser light is capable of being emitted only at the side of the optical fiber 1. The reflecting portion 13 is provided on a supporting member 14 at the end of the stainless-steel tube 2, and the reflecting portion 13 is made of a reflecting material such as a layer of gold plating positioned inside the supporting member 14.

The emitting portion L is formed in a U-shape in the above-described embodiments, when it is observed from the left side in FIG. 2. Portion L, however, may be a circle or a trapezium or a rectangle (the top of every shape needs to remain discontinuous).

Figure 7:
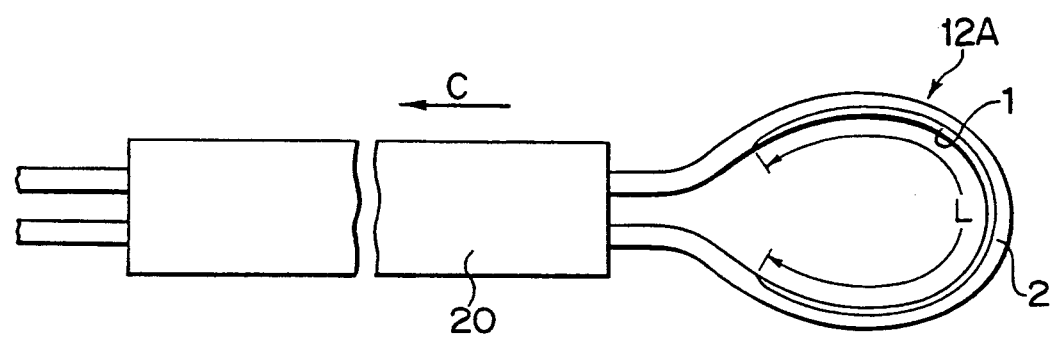
FIG. 7 is a plan view of the third embodiment of a laser light emitter according to the present invention.
Figure 11:
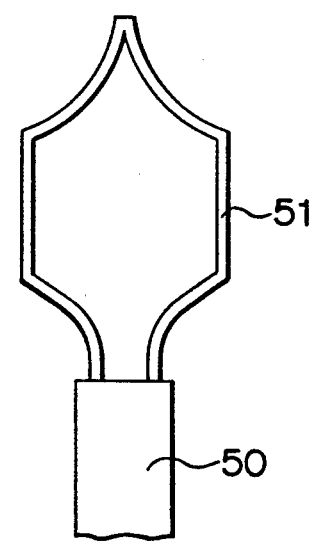
FIG. 11 is a plan view of a conventional apparatus.

On the other hand, FIG. 7 shows a plan view of the third embodiment which uses a ring-shaped portion 12A formed at the end of a holder 20. A part of stainless-steel tube 2 is broken away and the core of the optical fiber 1 is exposed as shown in the first embodiment.

In the third embodiment, the ring-shaped portion 12 is so positioned that the prominence is disposed within the ring-shaped portion 12A like a conventional snare, and then the ring-shaped portion 12A is moved in the direction C to perform excision by laser light irradiation.

In the third embodiment, the holder 20 can be omitted.

In the above-described embodiments, the emitting portion is formed on almost the whole of the ring-shaped portion 12 or 12Ax; however, in the first embodiment the emitting portion can be formed only at the bottom of the U-shaped portion and in the third embodiment the emitting portion can be formed only on the inside half of the ring shaped portion.

Moreover, in the above-described embodiments, the core of the optical fiber is covered with a metal material, for example stainless-steel tube, provide strength. However, if so much strength is not needed, a light emitter can be formed of a single optical fiber covered with cladding wherein the cladding partly broken away and the core is exposed to form the emitting portion. In this case, the clad is equivalent to the light emission-intercepting portion in the present invention.

Figure 8:
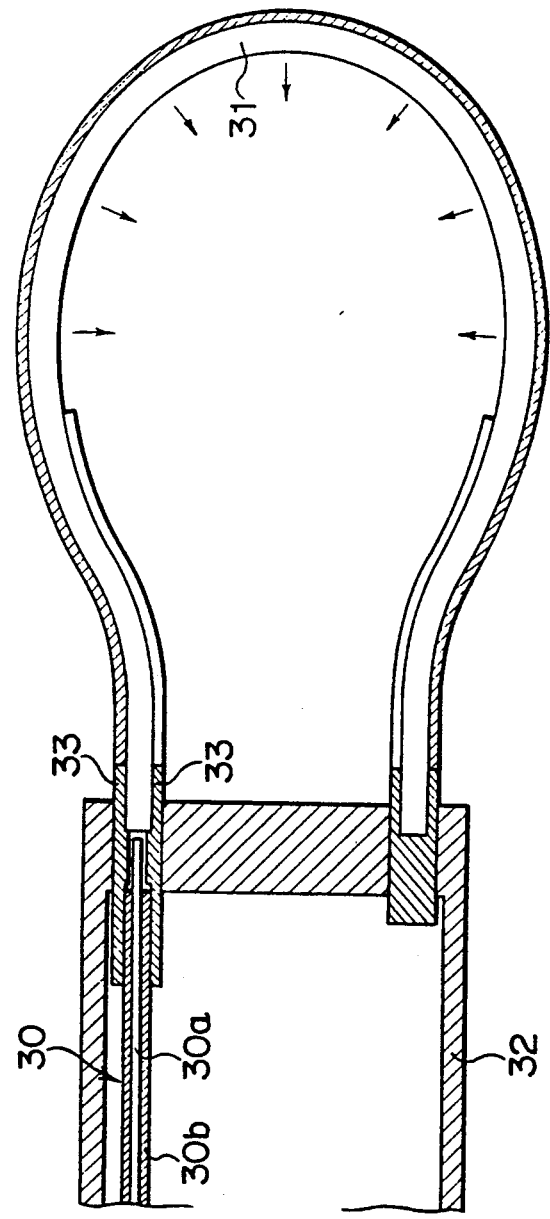
FIG. 8 and FIG. 9 are perspective views of still other enbodiments.

Moreover, in a modification of the third embodiment illustrated in FIG. 8, an emitting member 31 made of a light-transmissible ceramic, for example bent into ring-shape having circular cross section, is provided at the end of an optical fiber 30 having a core 30a and a cladding 30b, and laser light exited at the end of the core 30a of the optical fiber 30 enters into the emitting member 31, and then laser light is capable of being emitted from the emitting member 31. The part designated by numeral 32 is a holder, and the part designated by numeral 33 is the instrument for connecting. Such a method of providing indirect incidence is applicable in the first embodiment and in the second embodiment.

Figure 1:
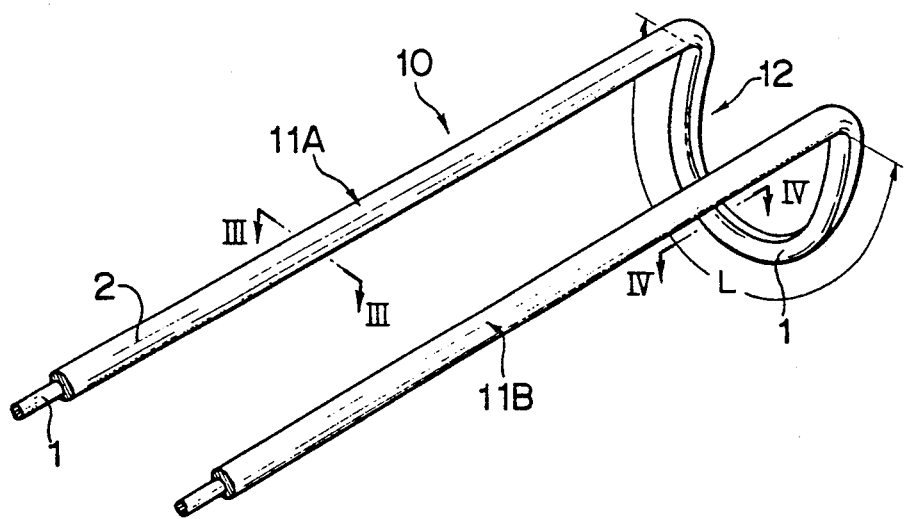
FIG. 1 is a perspective view of the first embodiment of a laser light emitter according to the present invention.
Figure 9:
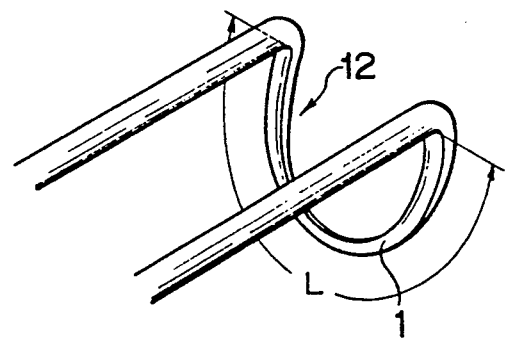
Figure 10:
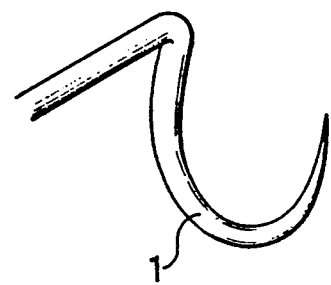
FIG. 10 is a vertical sectional view of another embodiment, wherein laser light is emitted through a light-transmissible ceramic material provided at the end of an optical fiber.

On the other hand, as shown in FIG. 9 and FIG. 10 respectively corresponding to FIG. 1 and FIG. 5, if laser light is to be emitted with higher concentration in to the direction for excision, the core 1 is formed so that its diameter gradually gets thinner. Then the quantity of emitted laser light increases at the diminished portion as with the case of a slender conic probe, so the laser light can be led to the direction for excision more effectively.

On the other hand, the surface of a laser light emitting portion can be provided with a surface layer for diffusing of laser light if needed. Laser light absorbing particles, such a carbon, or a laser light diffusing particles, such as silica having a larger refractive index than that of an emitting member core material, can be utilized. Also, the surface of a laser light emitting portion can be provided with a roughened surface to raise diffusing.

In this disclosure, there are shown and described only the preferred embodiments of the invention, but, as aforementioned, it is to be understood that the invention is capable of use in various other combinations and environments and is capable of changes or modifications within the scope of the inventive concept as expressed herein.

What is claimed is:

1. A laser light emitter for excision of protruding tissue of an animal organism, the emitter comprising:
    an optical transmission element having a holding portion through which light is transmitted into a bent portion that has an end surface and a side surface; and
    a light impervious material covering a first portion of said side surface of the bent portion of the optical transmission element, such that a second portion of said side surface of the bent portion of the optical transmission element is uncovered, whereby laser light applied to the optical transmission element will be emitted from the uncovered second portion of said side surface of the bent portion to impinge on and excise protruding tissue.

2. A laser light emitter according to claim 1, wherein the optical transmission element includes at least one straight portion connected to the bent portion.

3. A laser light emitter according to claim 2, wherein the bent portion is bent at an angle with respect to the at least one straight portion, and the uncovered second portion of said side surface of the bent portion emits laser light to perform the excision in a direction parallel to the at least one straight portion.

4. A laser light emitter according to claim 3, wherein an angle formed by the bent portion with respect to the at least one straight portion is between 45° and 120°.

5. A laser light emitter according to claim 1, wherein the bent portion is U-shaped, and the uncovered second portion of said side surface of the bent portion is located on one lateral side of the U-shape.

6. A laser light emitter according to claim 1, wherein the bent portion forms a curve and the uncovered second portion of said side surface of the bent portion is located along an inside part of the curve on the same side as the at least one straight portion of the optical transmission element.

7. A laser light emitter according to claim 1, wherein the bent portion tapers toward a distal end to the end surface thereat to form a narrow section such that the narrow section concentrates light emitted through the end surface.

8. A laser light emitter according to claim 1, wherein the optical transmission element comprises an optical fiber.

9. A laser light emitter according to claim 1, wherein the optical transmission element comprises a light-transmission ceramic.

10. A laser light emitter according to claim 1, wherein the optical transmission element comprises an optical fiber, and the light impervious material covering the optical transmission element comprises a cladding formed on the optical transmission element.

11. A laser light emitter according to claim 1, further comprising a reflective member located at the end surface at an end of the bent portion of the optical transmission element, for reflecting any light reaching the reflecting member through the bent portion back through the optical transmission element.

* * * * *